(12) United States Patent
Ding et al.

(10) Patent No.: US 8,440,238 B2
(45) Date of Patent: May 14, 2013

(54) **SULFATED DERIVATIVE OF *GASTRODIA ELATA* POLYSACCHARIDE, PREPARATION METHOD AND ANTITUMOR USE THEREOF**

(75) Inventors: Kan Ding, Shanghai (CN); Hong Qiu, Shanghai (CN)

(73) Assignee: Shanghai Institute Materia Medica, Chinese Academy of Sciences, Shanghai (CN)

( * ) Notice: Subject to any disclaimer, the term of this patent is extended or adjusted under 35 U.S.C. 154(b) by 110 days.

(21) Appl. No.: 12/998,169

(22) PCT Filed: Sep. 21, 2009

(86) PCT No.: PCT/CN2009/001060
§ 371 (c)(1),
(2), (4) Date: May 4, 2011

(87) PCT Pub. No.: WO2010/037252
PCT Pub. Date: Apr. 8, 2010

(65) Prior Publication Data
US 2011/0207921 A1    Aug. 25, 2011

(30) Foreign Application Priority Data
Sep. 24, 2008  (CN) .......................... 2008 1 0200407

(51) Int. Cl.
*A61K 36/00*    (2006.01)
(52) U.S. Cl.
USPC ..................................................... 424/725
(58) Field of Classification Search ........................ None
See application file for complete search history.

(56) References Cited

FOREIGN PATENT DOCUMENTS
CN    101367879 A    2/2009

OTHER PUBLICATIONS

Perk et al. Id family of helix-loop-helix proteins in cancer. Nature Rev 5:603-614, Aug. 2005.*
Qiu et al, "Structure elucidation and sulfated derivatives preparation of two α-D-glucans from *Gastrodia elata* B1. and their anti-dengue virus bioactivities", Carbohydrate Research, 342 (2007) 2230-2236.
Zhao et al, "Inhibited Effect of Organism Polysaccharide on Transplanting Cancer of Mice", w/English abstract, Journal of the CUN (National Sciences Edition), Nov. 2008, vol. 17, No. 4.
Liu et al, "Primary Research on Isolation, Purification and Character of Polysaccharide of *Gastrodia elata* BL", w/English abstract, ACTA Laser Biology Sinica, Aug. 2007, vol. 16, No. 4.
Zhu et al, "Optimization of Extraction Parameters for Polysaccharides of *Gastrodia elata* B1", w/English abstract, Lishizhen Medicine and Materia Medica Research, Apr. 2007, vol. 18, No. 4.
Jiang et al, "Extraction, Purification and Determination of Polysaccharide in *Gastrodia elata* ", w/English abstract, Journal of the CUN (Natural Sciences Edition), Nov. 2007, vol. 16, No. 4.

* cited by examiner

*Primary Examiner* — Wu-Cheng Winston Shen
*Assistant Examiner* — Yih-Horng Shiao
(74) *Attorney, Agent, or Firm* — Nixon & Vanderhye P.C.

(57) ABSTRACT

The present invention discloses a sulfated derivative of polysaccharide extracted from *gastrodia elata* BL., the preparation method thereof and the use thereof in preparing antineoplastic medicaments, wherein, the *gastrodia elata* polysaccharide has the following structure:

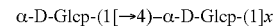

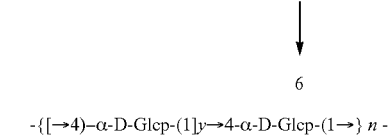

wherein, x and y are each an integer, and x+y=16,
"n" is and integer, and
the mean molecular weight of the polysaccharide from *gastrodia elata* is estimated as $2.8 \times 10^5$, the specific rotation of the polysaccharide is $+95°$ in a 0.5 mg/mL aqueous solution thereof;
the sulfated position is mainly at 6-hydroxy of the *gastrodia elata* polysaccharide, with mean molecular weight of $6.5 \times 10^4$ and a specific rotation of $+150.0°$ in a 0.5 mg/mL aqueous solution thereof. In vivo and in vitro experiments indicate that the sulfated derivative of *gastrodia elata* polysaccharide can inhibit the tumor growth by suppressing the expression of Id1 to inhibit angiogenesis, and therefore has an obvious antitumor activity, and shows almost nontoxicity to endothelial cells, thereby having a good prospect of being developed into antineoplastic medicaments.

1 Claim, 3 Drawing Sheets

SULFATED DERIVATIVE OF *GASTRODIA ELATA* POLYSACCHARIDE, PREPARATION METHOD AND ANTITUMOR USE THEREOF

This application is the U.S. national phase of International Application No. PCT/CN2009/001060, filed 21 Sep. 2009, which designated the U.S. and claims priority to CN Patent Application No. 200810200407.3, filed 24 Sep. 2008, the entire contents of each of which are hereby incorporated by reference.

TECHNICAL FIELD

The present invention relates to a sulfated derivative of *gastrodia elata* polysaccharide extracted from *gastrodia elata*, the preparation method thereof and the use thereof in preparing antineoplastic medicaments.

BACKGROUND OF THE INVENTION

Id1 is a member of the DNA-binding protein inhibitors of the bHLH transcription factor family, and locates in the nucleus. It is one of the essential factors for promoting angiogenesis. Id1 has a high expression in most tumors, and a low expression in normal tissues, and therefore is a well established target for antitumor therapeutic strategies, which makes it has been a hot spot in research and development of antineoplastic medicaments to develop an inhibitor with low-toxicity, high efficiency and strong specificity aimed at Id1. At present, it has been reported an antisense oligonucleotide Id1-PCAO specifically targeting endothelial cells and a small molecular cannabidiol inhibiting the expression of Id1 in invasive breast cancer cells. However, none of them is a good candidate for new drug development, since the antisense oligonucleotide as a drug still has many obstacles in technique, while cannabidiol is a cannaboid analogue.

*Gastrodia elata* BL. is a famous traditional Chinese materia medica, and at present, there is no formal report on a polysaccharide and polysaccharide derivatives thereof. The present inventors extract *gastrodia elata* polysaccharide from *gastrodia elata*, and further obtain a sulfated derivative (WSS25) thereof by sulfation of the polysaccharide. WSS25 at a dose of 25 μg/ml can almost completely suppress the expression of Id1 both at mRNA level and at protein level, and therefore can inhibit the growth of tumor by inhibiting the growth of blood vessels while being nearly nontoxic to endothelial cells, and thereby is an Id1 inhibitor having high efficiency and hypotoxicity.

DISCLOSURE OF THE INVENTION

Accordingly, one object of the present invention is to provide a sulfated derivative of *gastrodia elata* polysaccharide extracted from *gastrodia elata*, wherein, the *gastrodia elata* polysaccharide has the following structure:

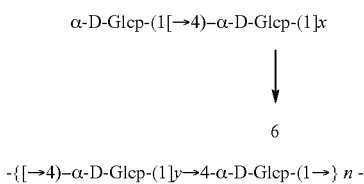

wherein, "x" and "y" are each an integer and x+y=16, "n" is an integer, the *gastrodia elata* polysaccharide has a mean molecular weight of $2.8 \times 10^5$ and a specific rotation of +95° in a 0.5 mg/mL aqueous solution thereof;

the sulfated derivative of the *gastrodia elata* polysaccharide is a derivative sulfated mainly at 6-hydroxy of the *gastrodia elata* polysaccharide, and has a mean molecular weight of $6.5 \times 10^4$ and a specific rotation of +150.0° in a 0.5 mg/mL aqueous solution thereof.

Another object of the present invention is to provide a method for preparing the sulfated derivative of *gastrodia elata* polysaccharide, comprising:

1) preparation of a water-extracted crude polysaccharide (WGE): after defatted by ethanol and dried, dry *gastrodia elata* slices are repeatedly extracted with hot water for 2 to 5 times; the combined extraction solution is concentrated, deproteinized by trichloroacetic acid, and centrifuged; the obtained supernatant is neutralized, dialyzed and concentrated to produce a concentrate; the concentrate is added with 2 to 5 volumes of ethanol, and centrifuged to produce a precipitate, which is then dried in vacuum to give a water-extracted crude polysaccharide (WGE);

2) preparation of a *gastrodia elata* polysaccharide (WGESC1A): the water-extracted crude polysaccharide from step 1) is dissolved in an appropriate amount of water and centrifuged; the supernatant is separated through column chromatography using diethylaminoethyl cellulose (DEAE-cellulose (type Cl⁻) as a carrier by gradient elution with water and 0.1 to 0.4 mol/L NaCl solution; the eluate from 0.1 mol/L NaCl solution is concentrated, dialyzed and lyophilized to produce the *gastrodia elata* polysaccharide as a white flocculent solid (WGESC1A);

3) preparation of a sulfated derivative of *gastrodia elata* polysaccharide (WSS25): after pyridine treated by molecular sieve is cooled down under an ice bath, chlorosulfonic acid is dropwisely added into the pyridine to prepare an esterifying agent; the *gastrodia elata* polysaccharide is dissolved in formamide treated by molecular sieve, and the solution is cooled down under an ice bath, followed by dropwise addition of the above prepared esterifying agent; after the reaction finishes, the reaction mixture is adjusted to a pH value at 7.8, and concentrated; the concentrate is dialyzed first with saturated NaHCO₃ solution, and then with water; the solution inside the dialysis tubing is lyophilized to produce the sulfated derivative of the *gastrodia elata* polysaccharide, WSS25.

More particularly, in the step 1), dry *gastrodia elata* crude slices are defatted by a 95 wt % ethanol for one week, and then naturally dried at room temperature; the dried *gastrodia elata* slices are repeatedly extracted by water at 100° C. until the extraction solution has no obvious reaction for the test of sulfuric acid-phenol; the extraction solutions for each time are combined and concentrated by heating; after cooled down, the resultant concentrate is deproteinized by a 15% (W/V) trichloracetic acid solution, and centrifuged; the resultant supernatant is adjusted to a pH value at 7.0 with a 1 mol/L NaOH solution, and then dialyzed against flowing water for 72 h; the solution inside the dialysis tubing is concentrated to a small volume, and added with 3 volumes of 95 wt % ethanol to stand overnight; the supernatant is discarded, and the remains are centrifuged; the obtained precipitate is washed with 2 volumes of anhydrous ethanol and acetone in sequence for dehydration, and then centrifuged; the resultant precipitate is dried in vacuum at 40° C. to produce a water-extracted crude polysaccharide, WGE.

in the step 2), the water-extracted crude polysaccharide, WGE, is dissolved in an appropriate amount of water, and centrifuged to remove the insoluble substances; the supernatant is separated through a DEAE-cellulose (type Cl⁻) column by gradient elution with water, 0.1 mol/L NaCl, 0.2 mol/L NaCl and 0.4 mol/L NaCl solution in sequence; an elution curve is plotted by using the sulfuric acid-phenol detection, and the eluates are pooled according to the elution curve, respectively; the eluate from 0.1 mol/L NaCl solution is concentrated, and dialyzed with distilled water; the solution inside the dialysis tubing is lyophilized to produce a *gastrodia elata* polysaccharide, WGESC1A.

in the step 3), after pyridine treated by 4 Å molecular sieve is cooled down under an ice bath, chlorosulfonic acid is dropwisely added in the pyridine with a ratio of the chlorosulfonic acid to pyridine of 2:1 in volume to produce an esterifying agent; 158.9 mg of *gastrodia elata* polysaccharide is dissolved in 8 mL of formamide treated by 4 Å molecular sieve, and the obtained solution is cooled down to 0° C. under an ice bath, followed by dropwise addition of 2 mL of the freshly prepared esterifying agent; after the addition, the reaction is performed under a water bath at 25° C. for 4 h; after the reaction finishes, the reaction mixture is adjusted to a pH value at 7.8 with a 5 mol/L NaOH solution, and then concentrated under reduced pressure at a temperature less than 30° C. to a small volume; the concentrate is dialyzed with 2 L of saturated $NaHCO_3$ solution for 24 h, and then with 2 L of deionized water, wherein the dialysis is carried out for 24 h each time with a total of 3 times; the solution inside the dialysis tubing is lyophilized to produce a sulfated derivative of the *gastrodia elata* polysaccharide. FIG. 2 is a $^{13}C$ NMR spectrum of WSS25, and it can be seen from FIG. 2 that the sulfation mainly takes place on the C-6 position.

In the above extraction process, the *gastrodia elata* crude slices were purchased from Shanghai Xuhui Herbal Medicine Co., Ltd. (Shanghai, China), the water might be distilled water or deionized water, and the dialysis tubing was the commonly used dialysis tubing in the art.

Still another object of the present invention is to provide use of the sulfated derivative of *gastrodia elata* polysaccharide in preparing antineoplastic medicaments. In vivo and in vitro experiments confirm that the sulfated derivative of *gastrodia elata* polysaccharide can inhibit the tumor growth by suppressing the expression of Id1 to inhibit angiogenesis, and therefore exhibits an obvious antitumor activity. Hence, the sulfated derivative of *gastrodia elata* polysaccharide has a good prospect of being developed into an antitumor medicament in the future.

BEST MODE FOR CARRYING OUT THE INVENTION

Example 1

Extraction of Polysaccharide from *gastrodia elata*

1000 g of dry *gastrodia elata* slices was defatted by 5 L of 95 wt % ethanol for one week, and then naturally dried at room temperature. 975 g of dried *gastrodia elata* slices was extracted by boiling water for 4 h with 30 L of water added each time. The content of saccharide in the extraction solution was determined by sulfuric acid-phenol method, and the extraction was performed until there was no obvious reaction for saccharide. The extraction solutions for each time were combined and concentrated to a small volume. The concentrate was deproteinized by a 15% (W/V) trichloracetic acid solution, and centrifuged. The resultant supernatant was adjusted to a pH value at 7.0 with a 1 mol/L NaOH solution, and then dialyzed against flowing water for 72 h. The solution inside the dialysis tubing was concentrated to a small volume, and added with 3 volumes of 95 wt % ethanol to stand overnight. The supernatant was discarded, and the remains were centrifuged. The obtained precipitate was washed with anhydrous ethanol and acetone in sequence for dehydration, and then centrifuged. The resultant precipitate was dried in vacuum at 40° C. to produce 195 g of water-extracted crude polysaccharide, WGE.

5 g of the water-extracted crude polysaccharide, WGE, was dissolved in an appropriate amount of water, and centrifuged to remove the insoluble substances. The supernatant was separated through a DEAE-cellulose (type Cl$^-$) column by elution with water, 0.1 mol/L NaCl, 0.2 mol/L NaCl and 0.4 mol/L NaCl solution in sequence. An elution curve was plotted by using the sulfuric acid-phenol detection, and the eluates were pooled according to the elution curve, respectively. The eluate from 0.1 mol/L NaCl solution was concentrated, and dialyzed with distilled water. The obtained solution inside the dialysis tubing was lyophilized to produce WGESC1A (2.0 g).

Determination of the physicochemical properties: according to conventional methods for polysaccharide, using dextrans T-700, T-580, T-110, T-80, T-40 and T-11 with known molecular weights as the standard, the mean molecular weight of WGESC1A was estimated as $2.8 \times 10^5$ on a Waters HPGPC, and a specific rotation of this polysaccharide is +95° in a 0.5 mg/mL aqueous solution thereof on a polarimeter of Perkin-Elmer 241 M.

Components analysis of polysaccharide: 2 mg of WGESC1A was hydrolyzed by trifluoroacetic acid (TFA) in a sealed tube at 110° C. for 1.8 h. The hydrolysates were acetylated and analyzed by using a Shimadzu GC-14B gas chromatograph. The results indicated that WGESC1A was a glucan.

Figure 1:
FIG. 1 is a $^{13}C$ NMR spectrum of WGESC1A.

Chemical structure assay: according to conventional methods for polysaccharide, 40 mg of WGESC1A was subjected to deuterium exchange, is and then analyzed on a Brucker AM-400 nuclear magnetic resonance analyzer to obtain a $^{13}C$ NMR spectrum thereof (see FIG. 1). According to Needs method, 8 mg of WGESC1A was subjected to a methylation analysis. The results indicated that the molar ratio of the terminal glucose, 1,4-linked glucose and 1,4,6-linked glucose in WGESC1A was 1:16:1, and therefore, WGESC1A was an alpha-1,4-linked glucan with a small amount of alpha-1,4-linked glycan at the C-6.

Example 2

Preparation of the Sulfated Derivative of *gastrodia elata* Polysaccharide

Figure 2:
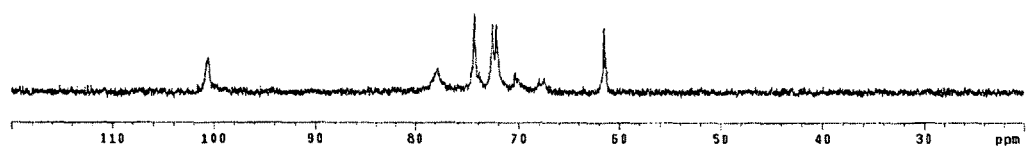
FIG. 2 is a $^{13}C$ NMR spectrum of WSS25.

After pyridine treated by 4 Å molecular sieve was cooled down under an ice bath, chlorosulfonic acid was dropwisely added in the pyridine with a ratio of the chlorosulfonic acid to pyridine of 2:1 in volume to produce an esterifying agent. 158.9 ml of *gastrodia elata* polysaccharide was dissolved in 8 mL of formamide treated by 4 Å molecular sieve, and the obtained solution was cooled down to 0° C. under an ice bath, followed by dropwise addition of 2 mL of the freshly prepared esterifying agent. After the addition, the reaction was performed under a water bath at 25° C. for 4 h. After the reaction finished, the reaction mixture was adjusted to a pH value at 7.8 with a 5 mol/L NaOH solution, and then concentrated under reduced pressure at a temperature less than 30° C. to a small volume. The concentrate was dialyzed with 2 L of saturated $NaHCO_3$ solution for 24 h, and then with 2 L of deionized water, wherein the dialysis was carried out for 24 h each time with a total of 3 times. The solution inside the dialysis tubing was lyophilized to produce a sulfated derivative of WGESCIA, WSS25. FIG. 2 is a $^{13}C$ NMR spectrum of WSS25, and it can be seen from FIG. 2 that the sulfation mainly takes place on the C-6 position.

Determination of physicochemical properties: according to conventional methods for polysaccharide, using dextrans T-700, T-580, T-110, T-80, T-40 and T-11 with known molecular weights as the standard, the mean molecular weight of WSS25 was estimated as $6.5 \times 10^4$ on a Waters HPGPC, and a specific rotation is +150.0° in a 0.5 mg/mL aqueous solution thereof on a polarimeter of Perkin-Elmer 241 M.

Experimental Example

1. Screening of Id1 Expression Inhibitors pGL4.14[luc2/Hygro] containing Id1 promoter region was transferred into human embryonic kidney cells HEK-293 (from American Type Culture Collection), and then screened with hygromycin to obtain a stable cell line Id1-luc/HEK293, which was used in screening of Id1 expression inhibitors and incubated with a DMEM medium containing 10% fetal calf serum (a product of Hangzhou Sijiqing Biological Engineering Materials Co., Ltd., China) in an incubator at 37° C. with 5% $CO_2$. In screening, 90 μL of Id1-luc/HEK293 cells was inoculated on a 96-well plate with 2,500 cells per well. 24 h later, 10 μL of 250 μg/mL and 1,000 μg/mL WSS25 were added, respectively. For each concentration, the test was carried out in triplicate wells, and included control wells containing normal saline in equal amount. After the culture continued for 18 h, the luciferase activity was measured on a luminometer (NOVOstar BMG LABTECH. Pty. Ltd), and inhibition was calculated according to the following equation:

Inhibition=[(relative luciferase activity of control group−relative luciferase activity of treated group)/relative luciferase activity of control group]×100%.

Figure 3:
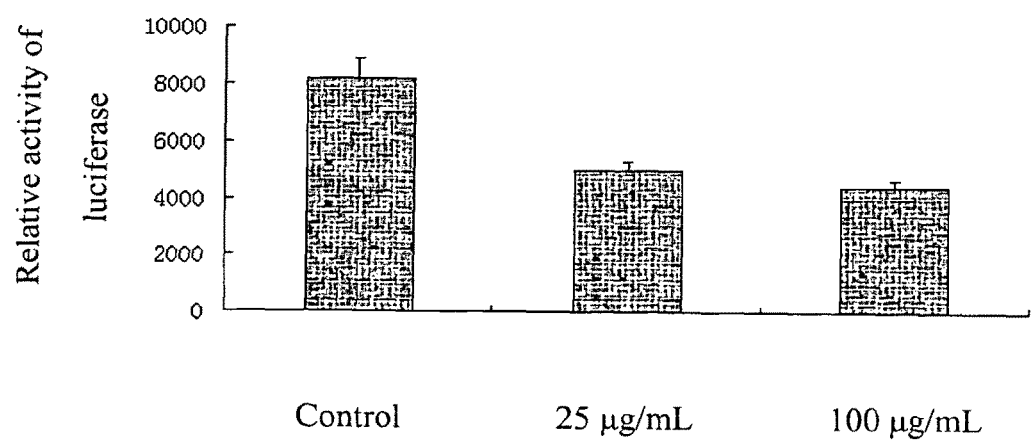
FIG. 3 is a graph illustrating the effect of WSS25 on the expression of luciferase in Id1-luc/HEK293 cells.

As shown in FIG. 3, the inhibition of WSS25 at 25 μg/mL and 100 μg/mL were 39.25% and 46.24%, respectively.

2. The Effect of WSS25 on Tube Formation of Human Microvascular Endothelial Cell (HMEC-1).

Figure 4:
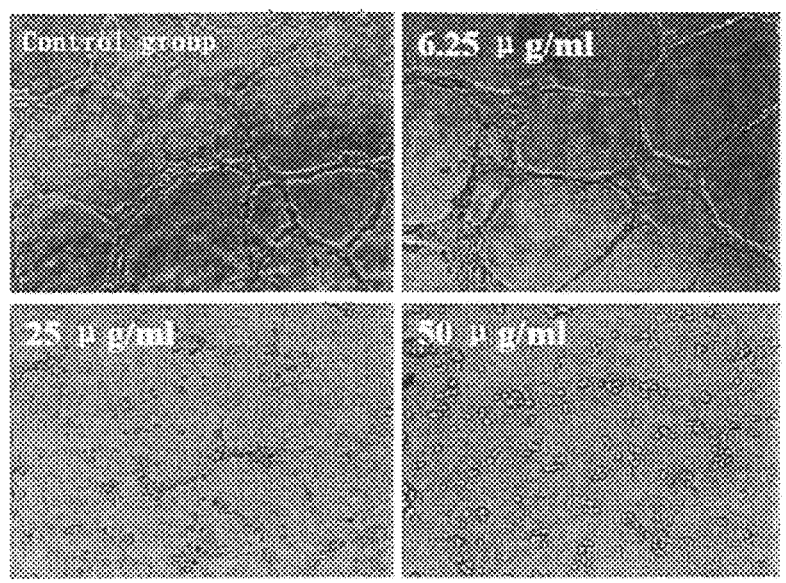
FIG. 4 is a picture demonstrating the inhibitory effects of WSS25 at different concentrations on tube formation of HMEC-1 cells on matrigel.

A 96-well plate was loaded with matrigel (BD Biosciences) with 50 μL per well, and kept at 37° C. for 30 min, and then were added 10 μL of WSS25 and 90 μL of medium containing $3 \times 10^4$ HMEC-1 cells such that the final concentrations of WSS25 were 6.25 μg/mL, 25 μg/mL and 50 μg/mL, respectively. For each concentration, the test was carried out in triplicate wells. The medium was a MCDB131 medium (Invitrogen, U.S.A.) containing 2 mM glutamine, 10 ng/mL EGF (Shanghai PRIMEGENE Bio-Tech Co., Ltd., Shanghai, China), 15% FBS (Hangzhou Sijiqing Biological Engineering Materials Co., Ltd., Hangzhou, China), 100 U/mL penicillin and 100 μg/mL streptomycin. The inoculated 96-well plate was incubated in an incubator at 37° C. with 5% $CO_2$ for 10 h, and then was taken pictures with magnification of 200 on a microscope (Olympus IX 51). As shown in FIG. 4, WSS25 at 25 μg/mL substantially suppressed the tube formation of HMEC-1 cells on matrigel, and at a low concentration also exhibited a weak inhibitory activity.

3. The Cytotoxicity of WSS25 on HMEC-1 Cells

Human microvasular endothelial HMEC-1 cells were incubated in a MCDB131 medium (product of Invitrogen) containing 2 mM glutamine, 10 ng/mL EGF (Shanghai PRIMEGENE Bio-Tech Co., Ltd, Shanghai, China), 15% FBS (Hangzhou Sijiqing Biological Engineering Materials Co., Ltd., Hangzhou, China), 100 U/mL penicillin and 100 μg/mL streptomycin, and 90 μL of HMEC-1 cells in good conditions was seeded on a 96-well plate with 5,000 cells per well, and incubated in a incubator at 37° C. with 5% $CO_2$ for 24 hour. Then each well was added in 10 μL WSS25 such that the final concentrations of WSS25 were 10, 50, 100, 500 and 1000 μg/mL respectively. For each concentration, the test was carried out in triplicate wells. After that, the 96-well plate was incubated in an incubator at 37° C. with 5% $CO_2$. 24 h, 48 h and 72 h, wells were added with 20 μL of 5 mg/mL MTT (a product of Sigma), respectively, and kept at 37° C. for 4 h. 100 μL of lysis solution (10% SDS-5% isobutanol-0.1M HCl) was added therein to lyse at 37° C. for 12~16 h. The absorbance ($A_{570}$) was measured at 570 nm and the inhibition of WSS25 was calculated according to the following equation:

Inhibition=[($A_{570}$ of control group−$A_{570}$ of treated group)/$A_{570}$ of control group]×100%.

Figure 5:
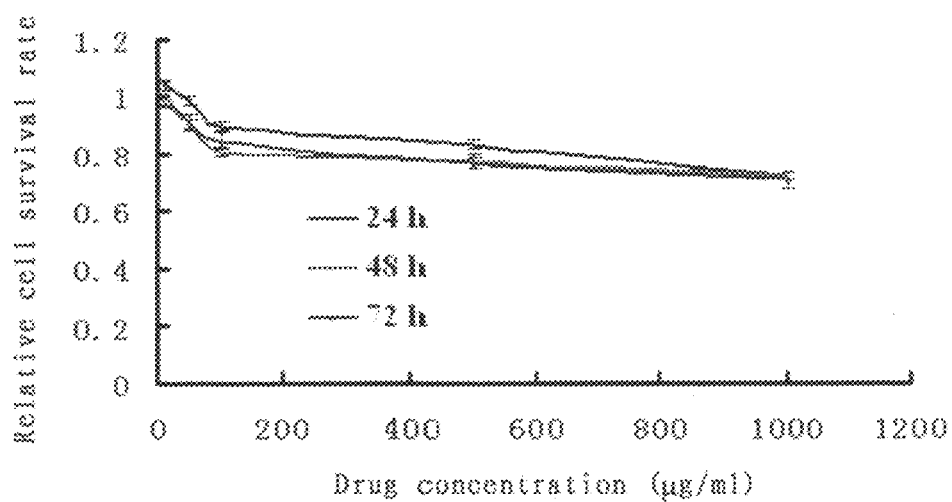
FIG. 5 is a graph illustrating the effects of WSS25 at different concentrations and under different treatment times on the growth of HMEC-1 cells.

Results showed that WSS25 at 1 mg/mL only had a weak cytotoxicity on endothelial cells, and at 100 μg/mL merely had no influence on them, as shown in FIG. 5.

4. The Inhibitory Effect of WSS25 Against the Growth of Xenograft on Nude Mice.

4.1 The Preparation of Drug to be Tested:

The drug to be tested in the present invention, WSS25, is a sulfated glucan, which was easily dissolved in water. In the experiment, WSS25 was formulated into solutions at different concentrations by using normal saline as a dissolvent. The solutions were administrated after filtered with a 0.22 μm micropore filter membrane.

4.2 Experiments on the Inhibitory Effect of WSS25 Against the Growth of Xenograft on Nude Mice.

4.2.1 Experiments on the Inhibitory Effect of WSS25 Against the Growth of Bel7402 Hepatoma Cells Xenograft on Nude Mice.

400 μL of cell suspension containing $4 \times 10^6$ Bel7402 hepatoma cells (from the committee on type culture collection, Chinese Academy of Sciences) was inoculated subcutaneously on right anterior limbs of BALB/cA nude male mice, which were 5-6 weeks old, and purchased from Shanghai SLAC Laboratory Animal Co. LTD. When the tumors grew up to a volume of about 100 $mm^3$ measured by a vernier caliper, the mice were randomly divided into a negative control group, and an administration group at 100 mg/kg WSS25, 5 mice in each group. Each mouse in the administration group was administered by 0.1 ml of prepared WSS25 per 10 g mouse bodyweight (the prepared WSS25 has a concentration at 10 mg/mL in freshly prepared with normal saline), while each mouse in the control group was administrated with an equivalent volume of normal saline. The administration was performed by caudal vein injection (the WSS25 was freshly prepared before the administration) every other day and last for 10 times. The mice were weighted each time before the administration. After the administration, the tumor volume was measured by a vernier caliper every 3 days, and calculated as follows:

Tumor volume(V)=0.52×$a$×$b^2$, wherein, "a" is the longest width of the xenograft, and "b" is the shortest width of the xenograft.

The mice were sacrificed at $21^{st}$ day, and as measured by a vernier caliper, the average tumor volume of the control group was 822.97 mm$^3$, and that of the administration group was 272.195 mm$^3$. Inhibition was calculated as follows:

Inhibition=[(tumor volume of control group−tumor volume of administration group)/tumor volume of control group]×100%

Figure 6:
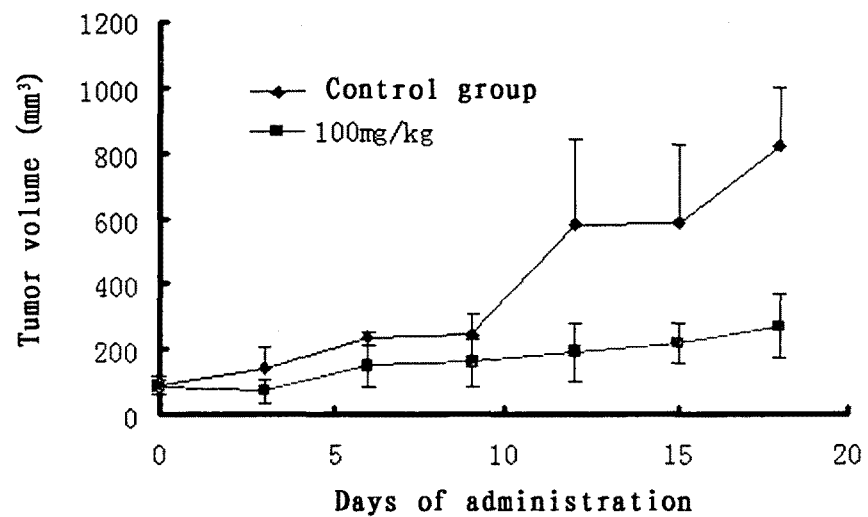
FIG. 6 is a graph illustrating the inhibitory effect of WSS25 on the growth of hepatoma Bel7402 cells transplanted on nude mice.

As shown in FIG. 6, the inhibition was 66.9%.

4.2.2 The Inhibitory Effect of WSS25 Against the Growth of Hepatoma SMMC7721 Cells Xenograft on Nude Mice 12 nude Balb/c male mice with a body weight of 23±1 g were provided by Shanghai SLAC Laboratory Animal Co. LTD. 1×10$^7$ human hepatoma SMMC-7721 cells (from the committee on type culture collection, Chinese Academy of Sciences) were inoculated subcutaneously in axillary fossa of the nude mice. After passed for 3 generations, the tumors were excised and cut into nubs of 1.5 mm$^3$, which were inoculated in the axillary fossa of the nude mice: When the xenograft grew up to about 100 mm$^3$ measured by a vernier caliper, the mice were randomly grouped and the administration started. The 12 nude mice inoculated with SMMC-7721 tumor cells were randomly divided into 2 groups, 6 in the negative control group, and 6 in the administration group (WSS25, 100 mg/kg). The mice in the negative group were administered with normal saline (0.1 mL/10 g) by caudal vein injection every other day, while the mice in the administration group (WSS25, 100 mg/kg) were administered with 10 mg/mL WSS25 solution (0.1 mL/10 g) (which was freshly prepared with normal saline before the administration) by caudal vein injection every other day. The mice were weighted and the tumor volume was measured by a vernier caliper every 3 days. The administration was stopped after administrated for 10 times. The body weight of mice in both of the negative group and the administration group (WSS25, 100 mg/kg) did not show significant changes before and after the experimental therapy, and no dead mouse were found in each of the groups. The mice were sacrificed at the $23^{rd}$ day and weighted, and the tumor volume were measured by a vernier caliper. The relative tumor volume (RTV) and the relative tumor growth rate (T/C) were calculated as follows.

Tumor volume (V)=$a$×$b^2$/2, wherein, "a" is the longest width of the xenograft and "b" is the shortest width thereof.

Relative tumor volume (RTV)=$V_t/V_0$, wherein, $V_t$ is the tumor volume at a given time and $V_0$ was the tumor volume measured when the mice were grouped;

The relative tumor growth rate T/C(%) was used as an evaluation index for the antitumor activity, T/C(%)=the average relative tumor volume of the administration group/the average relative tumor volume of the control group×100%. If T/C %≦60%, there is a statistically significant difference, which indicates an obvious antitumor activity in vivo.

Figure 7:
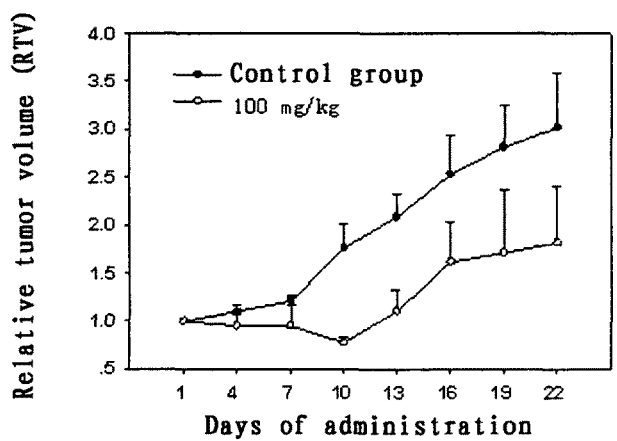
FIG. 7 is a graph illustrating the inhibitory effect of WSS25 on the growth of hepatoma SMMC7721 cells transplanted on nude mice.

Compared with the mice in the negative control group, the volume of xenograft on nude mice in the administration group (WSS25, 100 mg/kg) began to decrease from the $3^{rd}$ day after administration. As shown in FIG. 7, the relative tumor volume (RTV) of the negative control group was 3.0, while the RTV and the relative tumor growth rate (T/C) of the administration group (WSS25, 100 mg/kg) were 1.68 and 56% respectively.

As can be seen from the above experiments, the sulfated derivative of *gastrodia elata* polysaccharide prepared in the present invention, WSS25, exhibits a significant antineoplastic activity with almost nontoxicity to endothelial cells. Therefore it has a good prospect to be developed into antitumor medicaments.

The invention claimed is:

1. A method for treating a tumor in a subject in need thereof, the method comprising:
   administering to the subject in need thereof an effective amount of a sulfated derivative of *gastrodia elata* polysaccharide extracted from *gastrodia elata*, wherein the *gastrodia elata* polysaccharide has the following structure:

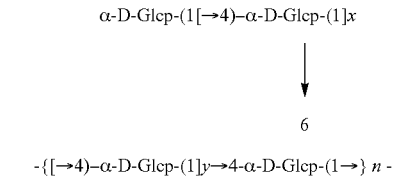

wherein
x and y are each an integer
x+y=16,
n is an integer,
the *gastrodia elata* polysaccharide has a mean molecular weight of 2.8×10$^5$ with a specific rotation of +95° in a 0.5 mg/mL aqueous solution thereof; and
the sulfated derivative of the *gastrodia elata* polysaccharide is a derivative sulfated mainly at the 6-hydroxy of the *gastrodia elata* polysaccharide with a mean molecular weight of 6.5×10$^4$ and a specific rotation of +150.0° in a 0.5 mg/mL aqueous solution thereof.

* * * * *

UNITED STATES PATENT AND TRADEMARK OFFICE
CERTIFICATE OF CORRECTION

PATENT NO. : 8,440,238 B2
APPLICATION NO. : 12/998169
DATED : May 14, 2013
INVENTOR(S) : Ding et al.

It is certified that error appears in the above-identified patent and that said Letters Patent is hereby corrected as shown below:

Title Page of Patent:

Delete

"(73) Assignee: Shanghai Institute Materia Medica, Chinese Academy of Sciences, Shanghai (CN)"

and insert therefor

--(73) Assignee: Shanghai Institute of Materia Medica, Chinese Academy of Sciences, Shanghai (CN)--.

Signed and Sealed this
Sixteenth Day of July, 2013

Teresa Stanek Rea
*Acting Director of the United States Patent and Trademark Office*